(12) United States Patent
Chuter (10) Patent No.: US 9,149,612 B2
(45) Date of Patent: Oct. 6, 2015

(54) FLEXIBLE HIGH-PRESSURE BALLOONS

(71) Applicant: West Coast Catheter, Inc., San Francisco, CA (US)

(72) Inventor: Timothy A. M. Chuter, San Francisco, CA (US)

(73) Assignee: WEST COAST CATHETER, INC., San Francisco, CA (US)

( * ) Notice: Subject to any disclaimer, the term of this patent is extended or adjusted under 35 U.S.C. 154(b) by 0 days.

(21) Appl. No.: 14/493,248

(22) Filed: Sep. 22, 2014

(65) Prior Publication Data

US 2015/0133988 A1 May 14, 2015

Related U.S. Application Data

(63) Continuation-in-part of application No. 14/280,328, filed on May 16, 2014.

(60) Provisional application No. 61/933,708, filed on Jan. 30, 2014, provisional application No. 61/962,314, filed on Nov. 13, 2013.

(51) Int. Cl.
*A61M 25/10* (2013.01)

(52) U.S. Cl.
CPC ......... *A61M 25/104* (2013.01); *A61M 25/1002* (2013.01); *A61M 2025/1084* (2013.01)

(58) Field of Classification Search
CPC .............. A61M 25/10; A61M 25/104; A61M 25/1002; A61M 2025/1084; A61F 2/958; A61F 2/86; A61F 2/90; A61B 2025/1081
See application file for complete search history.

(56) References Cited

U.S. PATENT DOCUMENTS

| | | |
|---|---|---|
| 3,674,014 A | 7/1972 | Tillander |
| 4,448,195 A | 5/1984 | LeVeen et al. |
| 4,637,396 A | 1/1987 | Cook |
| 4,706,670 A | 11/1987 | Andersen et al. |
| 4,762,130 A | 8/1988 | Fogarty et al. |
| 5,181,911 A | 1/1993 | Shturman |

(Continued)

FOREIGN PATENT DOCUMENTS

| | | |
|---|---|---|
| EP | 0186267 | 9/1990 |
| EP | 0388486 | 9/1990 |

(Continued)

OTHER PUBLICATIONS

International Search Report and Written Opinion dated Dec. 5, 2014 in International Application No. PCT/US2014/056159 filed Sep. 17, 2014, (14 pages).

*Primary Examiner* — Alexander Orkin
(74) *Attorney, Agent, or Firm* — William A. English; Vista IP Law Group LLP (57) ABSTRACT

Flexible high-pressure angioplasty balloons are disclosed herein which utilize an inflatable balloon positioned upon the catheter and a supporting structure secured over or along the catheter at a first location proximal to the balloon and at a second location distal to the balloon. Inflation of the balloon reconfigures the supporting structure to urge the first location and the second location towards one another thereby inhibiting longitudinal elongation of the balloon relative to the catheter. The supporting structure may surround, support, or otherwise extend over the entire length of the balloon and allows for the balloon to bend or curve even at relatively high inflation pressures.

20 Claims, 8 Drawing Sheets

(56) References Cited

U.S. PATENT DOCUMENTS

| | | |
|---|---|---|
| 5,484,411 A | 1/1996 | Inderbitzen et al. |
| 5,772,681 A | 6/1998 | Leoni |
| 5,868,779 A | 2/1999 | Ruiz |
| 6,129,706 A | 10/2000 | Janacek |
| 6,156,254 A | 12/2000 | Andrews et al. |
| 6,527,739 B1 | 3/2003 | Bigus et al. |
| 6,679,860 B2 | 1/2004 | Stiger |
| 6,695,809 B1 | 2/2004 | Lee |
| 6,746,425 B1 | 6/2004 | Beckham |
| 7,182,779 B2 | 2/2007 | Acosta et al. |
| 7,186,237 B2 | 3/2007 | Meyer et al. |
| 7,309,324 B2 | 12/2007 | Hayes et al. |
| 7,335,184 B2 | 2/2008 | Laguna |
| 7,354,419 B2 | 4/2008 | Davies, Jr. et al. |
| 7,635,510 B2 | 12/2009 | Horn et al. |
| 7,641,844 B2 | 1/2010 | Melsheimer |
| 7,682,335 B2 | 3/2010 | Pepper et al. |
| 7,686,824 B2 | 3/2010 | Konstantino et al. |
| 7,785,290 B2 | 8/2010 | Alpini et al. |
| 7,914,487 B2 | 3/2011 | Davies, Jr. et al. |
| 7,955,350 B2 | 6/2011 | Konstantino et al. |
| 8,002,741 B2 | 8/2011 | Hayes et al. |
| 8,221,351 B2 | 7/2012 | Pepper et al. |
| 8,672,990 B2 | 3/2014 | Holman et al. |
| 2001/0008970 A1 | 7/2001 | Ravenscroft et al. |
| 2002/0038141 A1* | 3/2002 | Yang et al. .............. 623/1.12 |
| 2002/0161388 A1* | 10/2002 | Samuels et al. ............ 606/192 |
| 2004/0243158 A1 | 12/2004 | Konstantino et al. |
| 2005/0021070 A1 | 1/2005 | Feld et al. |
| 2005/0021071 A1 | 1/2005 | Konstantino et al. |
| 2005/0177130 A1 | 8/2005 | Konstantino et al. |
| 2006/0271093 A1* | 11/2006 | Holman et al. ............ 606/194 |
| 2009/0038752 A1 | 2/2009 | Weng et al. |
| 2010/0234875 A1 | 9/2010 | Allex et al. |
| 2011/0238105 A1 | 9/2011 | Gelbart et al. |
| 2012/0296363 A1 | 11/2012 | Davies, Jr. et al. |

FOREIGN PATENT DOCUMENTS

| | | |
|---|---|---|
| EP | 0851777 | 7/1998 |
| EP | 1008363 | 6/2000 |
| EP | 1424962 | 6/2004 |
| EP | 2462975 | 6/2012 |
| WO | 8700442 | 1/1987 |
| WO | 9420166 | 9/1994 |
| WO | 9640350 | 12/1996 |

* cited by examiner

FLEXIBLE HIGH-PRESSURE BALLOONS

RELATED APPLICATION DATA

This application is a continuation-in-part of co-pending application Ser. No. 14/280,328, filed May 16, 2014, which claims benefit of application Ser. Nos. 61/933,708, filed Jan. 30, 2014 and 61/962,314, filed Nov. 13, 2013, the entire disclosures of which are expressly incorporated by reference herein.

FIELD OF THE INVENTION

The present invention relates to balloon catheters and to methods for making and using such balloon catheters. More particularly, the present invention relates to angioplasty catheters including balloons that maintain their flexibility when inflated and to methods for making and using such catheters.

BACKGROUND

Conventional angioplasty balloons are typically constructed of low-compliance materials that tolerate high inflation pressures and attain uniform predictable diameters in vivo even when portions of the surrounding artery are narrow and calcified. The typical balloon has a cylindrical section of uniform diameter between conical ends and a central catheter extending along the longitudinal axis of the balloon. When inflated at high-pressures, the walls of the balloon are placed into tension and the balloon generally loses its capacity for differential lengthening and hence becomes stiff and biased into a straightened configuration. Such balloons impose this straightened cylindrical configuration on any balloon-expanded stent that is crimped or otherwise loaded upon the balloon for expansion.

The presence of a straight stent in a curved artery (e.g., coronary, renal, femoral arteries, and the like) imparts stresses and strains into the stent structure, the artery, or both, especially when the artery is mobile. The resulting repetitive micro-trauma may incite inflammation, hyperplasia and recurrent narrowing, often to the point of catastrophic flow limitation.

Previous efforts to imbue an angioplasty balloon with flexibility have employed segmentation, helical shape, and compliant balloon materials. Segmented balloons take a variety of forms depending on the degree of segmentation. For instance, previous devices have included spherical balloons strung out along a central catheter having narrow intervening segments that are easily bent. However, such balloons are ill-suited to stent delivery because they impose a bumpy segmented shape upon the stent. If a segmented balloon is inflated enough to eliminate inter-segment gaps and deliver a more completely expanded stent, adjacent segments interfere with one another hindering much of the flexibility.

Other suggested balloons have included adjacent segments that are separated by grooves in an otherwise continuous balloon. These localized "hinge-points" do little to enhance differential lengthening and the effect on balloon flexibility is therefore modest at best. Other balloons have deep grooves that separate bulges in the balloon profile but these too have a modest effect on flexibility.

Helical balloons have also been used to increase flexibility where the winding of the balloon disrupts longitudinal continuity so that adjacent windings on the outer aspect of a bend in the balloon can separate while those on the inner aspect remain in close apposition. The resulting potential for differential lengthening imparts some flexibility. In addition, helical balloons benefit from multi-lumen construction. Each of the component balloons is narrower and therefore more flexible than the resulting helix. However, such helical balloons suffer many of the same limitations as segmented balloons. They either deliver incompletely expanded stents or become less flexible when overinflated to eliminate gaps. Moreover, even when the balloon is straight, its components have tight bends that, unless tightly constrained, straighten on high-pressure inflation, whereupon the helical balloon may tear itself apart. A non-compliant, tightly-wound, helical balloon may potentially tear itself apart upon high-pressure inflation. A less tightly wound helical balloon is more stable but less flexible.

Balloons that are constructed from compliant materials are more flexible than similar balloons constructed of non-compliant materials. However, compliant balloons cannot withstand the high pressures required for balloon angioplasty because they tend to expand in the direction of least resistance, leaving narrow areas untreated, rupturing the artery in areas of weakness, and/or spreading beyond the intended field of angioplasty. In addition, compliant balloons may be unable to generate sufficient force to initiate stent expansion. Early angioplasty balloons made of compliant materials were subsequently reinforced by the application of various braids, meshes, and wraps in an attempt to control balloon shape and dimensions at higher working pressures.

External braids, wraps, and fabrics of all kinds have also been embedded into the walls of low-compliance balloons to further increase the maximum working pressure. However, the integration of a braid into the low-compliance wall of a high-pressure balloon prevents changes in braid angle. The braid of such a balloon is not free to open and close, or shorten and lengthen, with balloon expansion and contraction. Consequently, the presence of the braid does nothing to shorten the balloon, relieve longitudinally-directed wall tension, generate redundant folds in its walls, or enhance balloon flexibility.

Accordingly, there exists a need for balloons that, when inflated to high-pressure, retain dimensional stability and flexibility.

SUMMARY

The present invention is directed to balloon catheters, and, more particularly, to angioplasty balloon catheters that include non-compliant balloons that maintain flexibility when inflated, and to methods for making and using such balloon catheters.

In an exemplary embodiment, an inflatable angioplasty balloon may be configured to include a supporting structure such as a braid, wrap, mesh, and the like, which is carried by the balloon membrane, e.g., wrapped around or otherwise positioned externally of the balloon membrane. The supporting structure may allow the balloon to retain increased flexibility when inflated such that the balloon is able to bend or curve even at relatively high inflation pressures.

Generally, the balloon assembly may include a catheter having a length, an inflatable balloon, e.g., with a substantially cylindrical mid-portion between two substantially conical or otherwise tapered end sections, positioned upon the catheter, e.g., on a distal portion of the catheter, and a supporting structure secured over or along the catheter at one or more locations, e.g., at a first location proximal to the cylindrical section of the balloon and at a second location distal to the cylindrical section of the balloon such that inflation of the balloon reconfigures the supporting structure to urge the first location and the second location towards one another thereby inhibiting longitudinal elongation of the balloon relative to the catheter.

During balloon expansion, the increasing balloon diameter may force the wires, fibers, or other elements of the supporting structure to deviate away from the most direct path between the first and second locations or other balloon attachments. Since the fibers of the supporting structure have little capacity for stretching, balloon-induced widening of the supporting structure has to be accompanied by shortening, which pulls the proximal and distal ends of the balloon towards one another. Hence, as the balloon inflates, tension imparted into these fibers substitutes or offsets the longitudinally-directed tension in the membrane wall of the cylindrical portion of the balloon. Further inflation may even produce one or more small redundant circumferential folds in the balloon. The combination of redundancy and low longitudinally-directed wall tension makes the balloon flexible, even when fully inflated.

In one exemplary embodiment, the supporting structure is external to the balloon membrane and freely movable relative to the balloon surface. In other variations, the supporting structure may be adhered or placed upon a surface of a thin elastic layer covering the balloon, sandwiched between adherent layers of the balloon, and the like. Furthermore, while a single helically wound fiber may be used, other variations may utilize multiple fibers (e.g., two or more) configured into a braid, wrap, mesh, and the like.

A supporting structure configured as a mesh of supporting fibers may bend in much the same way as a braided stent by reorienting its fibers rather than stretching its fibers. Moreover, the supporting fibers may offer little resistance to bending or curving of the balloon because little energy is needed to reorient such a mesh of fibers. Furthermore, increasing the number of fibers in a supporting structure configured as a braid, wrap, or mesh may reduce or eliminate bulging by portions of the balloon in the spaces between the fibers, e.g., by reducing the distance between the fibers and/or by further distributing any loads over the fibers.

Regardless of the number of fibers used or the configuration of the supporting structure, the supporting structure may be formed from substantially inelastic material (e.g., nylon, Nitinol, Kevlar Vectraon, Spectra, Dacron, Dyneema, Terlon (PBT), Zylon (PBO), Polyimide (PIM), ultra-high molecular weight polyethylene, and the like), shaped into fibers that are suitably flexible to be collapsed into a low-profile configuration when the balloon is deflated, e.g., for stent loading and/or intravascular delivery. The supporting structure is also suitably flexible to be reconfigured into its deployed configuration when the balloon is inflated for stent deployment or an angioplasty procedure.

Where the supporting structure comprises two or more fibers, these may slide freely where they intersect, or they may be attached or connected to one another at one or more intersection points.

The pitch or angle between the fibers of the supporting structure and the longitudinal axis of the balloon may vary according to the desired mechanical properties of the specific application. For example, a relatively low pitch—with the fibers initially oriented substantially parallel to the longitudinal axis of the balloon—may minimize resistance to expansion. A relatively high pitch substantially orthogonal to the longitudinal axis may optimize the flexibility of the fully expanded balloon, and/or place a finite upper limit on its diameter. The higher pitch may also increase the ratio of length change to diameter during expansion. The pitch may also vary along the length of a single balloon. For example, a relatively low pitch within the end sections may stabilize their shape and length, while a relatively high pitch in the cylindrical section may afford greater flexibility.

As the balloon shortens under the action of the supporting structure, a portion of the catheter within the balloon may also be configured to shorten, e.g., to accommodate the balloon shortening. In an exemplary embodiment, a supportive braid, wrap, or spring component of the catheter may prevent buckling, prevent collapse of the wire lumen, and/or, via its attachments to the supporting structure, help the balloon resume a low-profile state for removal.

In accordance with one embodiment, an apparatus is provided for performing procedure within a patient's body that includes a tubular member comprising a proximal end, a distal end sized for introduction into a patient's body, and a longitudinal axis extending therebetween; a non-compliant balloon carried on the distal end comprising a central region and end regions transitioning from the central region to attachment locations on the distal end, the balloon expandable from a contracted condition to an expanded condition; and a supporting structure comprising one or more substantially inelastic fibers extending helically around an outer surface of the balloon and comprising ends attached to the distal end such that the one or more fibers are movable relative to the central region of the balloon.

In accordance with another embodiment, a method is provided for performing a medical procedure that includes introducing a distal end of a tubular member into a patient's body with a non-compliant balloon thereon in a contracted condition and one or more inelastic fibers on the balloon in a low-profile configuration; positioning the balloon within a lesion within a body lumen; and expanding the balloon to an expanded condition, thereby reconfiguring the one or more fibers to shorten the balloon as the balloon expands.

In accordance with another embodiment, a method is provided for making a catheter that includes providing a tubular member comprising a proximal end and a distal end sized for introduction into a patient's body; forming a balloon from non-compliant material such that the balloon includes a central cylindrical section expandable to a predetermined size when inflated; attaching end sections of the balloon to the distal end of the tubular member; folding or rolling the balloon around the distal end into a contracted condition; wrapping one or more fibers around the balloon in the contracted condition; and attaching ends of the one or more substantially inelastic fibers adjacent the end sections of the balloons, the one or more fibers have predetermined length such that, upon inflation of the balloon, the one or more fibers apply an axially compressive force to shorten the balloon to enhance flexibility of the fully inflated balloon. In an exemplary embodiment, the fibers may be braided around the balloon such that the fibers are free to slide or otherwise move over the outer surface of the balloon, e.g., to accommodate bending the balloon. Alternatively, the outer surface of the balloon may have a relatively high friction finish to enhance engagement between the fibers and the balloon as the balloon is expanded.

In accordance with yet another embodiment, a method is provided for preparing a balloon catheter comprising a tubular member including proximal and distal ends, a non-compliant balloon on the distal end in a contracted condition and a plurality of inelastic fibers on the balloon in a low-profile configuration. The balloon may be inflated to an expanded condition, thereby reconfiguring the fibers to shorten the balloon as the balloon expands. For example, the fibers may be provided in a braid or mesh over the balloon such that the fibers are free to slide over the outer surface of the balloon, e.g., to accommodate bending of the balloon. Once expanded, the balloon may be bent into a curved shape in the expanded condition, thereby reconfiguring the fibers further to maintain the balloon in the curved shape. For example, the fibers may slide along the outer surface of the balloon to accommodate the curved shape and/or one or more folds may be formed in the balloon. The balloon may then be deflated to the contracted condition, e.g., such that the balloon is biased to the curved shape when subsequently re-inflated.

In an exemplary embodiment, the fibers may migrate over the outer surface of the balloon as the balloon is bent into the curved shape, e.g., such that fibers migrate towards the inside of the curve and/or otherwise reduce tension on the balloon and/or tubular member, which may facilitate the balloon bending without kinking. For example, the fibers may migrate towards the inside of the curve, creating an asymmetrical tension in the fibers that applies a similar asymmetrical force on the balloon to maintain the curved shape, regardless of externally applied bending forces that might otherwise cause the balloon to straighten. Thus, a balloon of this type may exhibit "shape-memory"—once inflated in a curved shape, the balloon may return to substantially the same curved shape when re-inflated, even though the uninflected balloon is straight and flexible. This phenomenon may occur because asymmetrical braid distribution only affects the shape of the balloon when the fibers are tensioned by balloon expansion. When the balloon is in its unexpanded state the braid fibers have little tension and exert little influence on balloon shape. In another embodiment, the braid may be configured to remain substantially stable, e.g., uniformly distributed over the outer surface independent of the shape to which the balloon is directed. Thus, in this embodiment, the fibers may slide easily over the outer surface as the balloon changes shape under the action of externally applied forces.

For example, if the balloon is prepared in preparation for a medical procedure, the distal end of the catheter may be introduced into a patient's body with the balloon in the contracted condition, and positioned within a lesion or other treatment side within a body lumen. The balloon may then be inflated within the body lumen, whereupon the balloon is biased towards the curved shape within the lesion. For example, the contracted balloon may be positioned within a curved body lumen and oriented such that the curved shape is aligned generally with the curved shape of the body lumen. Thus, when the balloon is inflated, the balloon may expand towards the curved shape, thereby dilating the body lumen while minimizing risk of straightening or otherwise imposed undesired stresses on the walls of the body lumen.

Other aspects and features including the need for and use of the present invention will become apparent from consideration of the following description taken in conjunction with the accompanying drawings.

BRIEF DESCRIPTION OF THE DRAWINGS

It will be appreciated that the exemplary apparatus shown in the drawings are not necessarily drawn to scale, with emphasis instead being placed on illustrating the various aspects and features of the illustrated embodiments. The drawings illustrate exemplary embodiments, in which.

DETAILED DESCRIPTION OF THE EXEMPLARY EMBODIMENTS

Generally, the apparatus and methods herein relate to catheters for performing angioplasty and/or other endovascular procedures and/or for otherwise treating body lumens within a patient's body, e.g., including a catheter or other tubular member carrying a balloon that includes a proximal end section and a distal end section (e.g., conically-shaped or otherwise tapered end sections) and having a substantially cylindrical section therebetween. The balloon also includes a supporting structure such as one or more wires or other fibers provided as a braid, wrap, mesh, and the like, which is wrapped around the balloon membrane. The supporting structure may surround, support, and/or otherwise extend over the entire length of the balloon to provide support yet be free to move relative to the balloon, which may allow the balloon to retain increased flexibility and/or enable the balloon to bend or curve and/or resist straightening from a curved shape even at relatively high inflation pressures. If the balloon includes a high-friction outer surface, the supporting structure may engage the balloon upon inflation, thereby resisting the balloon changing shape from the shape before it is inflated, e.g., a curved or other non-straight shape corresponding to the body lumen where the balloon is deployed.

During balloon expansion, the increasing balloon diameter may force the fibers of the supporting structure apart from one another, thereby shortening the supporting structure along its longitudinal axis. This shortening of the supporting structure pulls the proximal and distal ends of the balloon towards one another. Hence, as the balloon itself becomes fully inflated, tension imparted into these fibers substitutes or offsets the longitudinally-directed tension in the membrane wall of the cylindrical portion of the balloon. Thus offloaded, the membrane walls of the cylindrical portion of the balloon are free to lengthen differentially thereby allowing for balloon curvature and/or increased flexibility even when fully inflated.

Figure 1A:
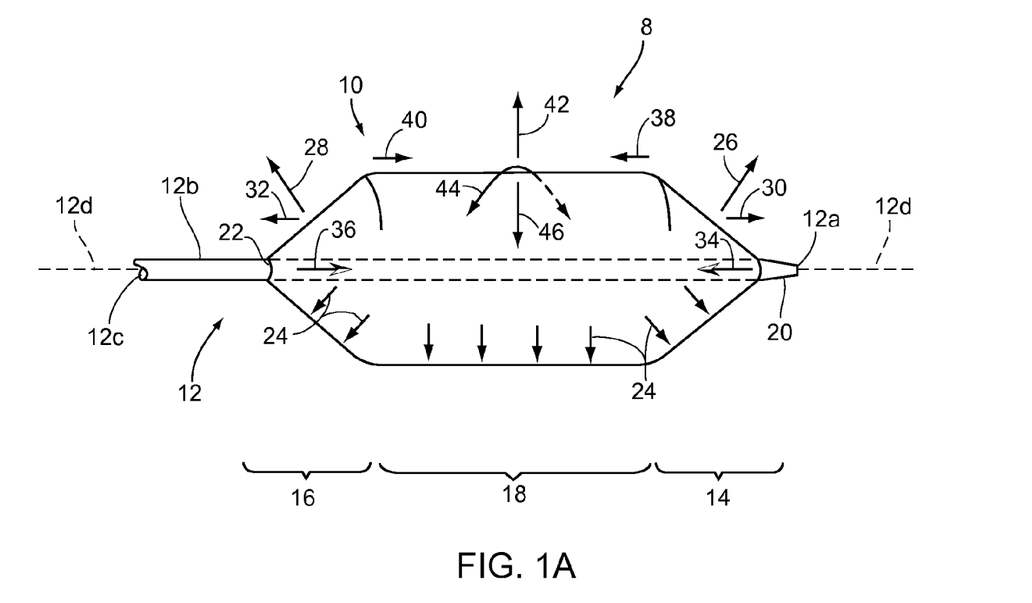
FIG. 1A shows a side view of one example of an angioplasty balloon positioned upon an elongate catheter.
Figure 1B:
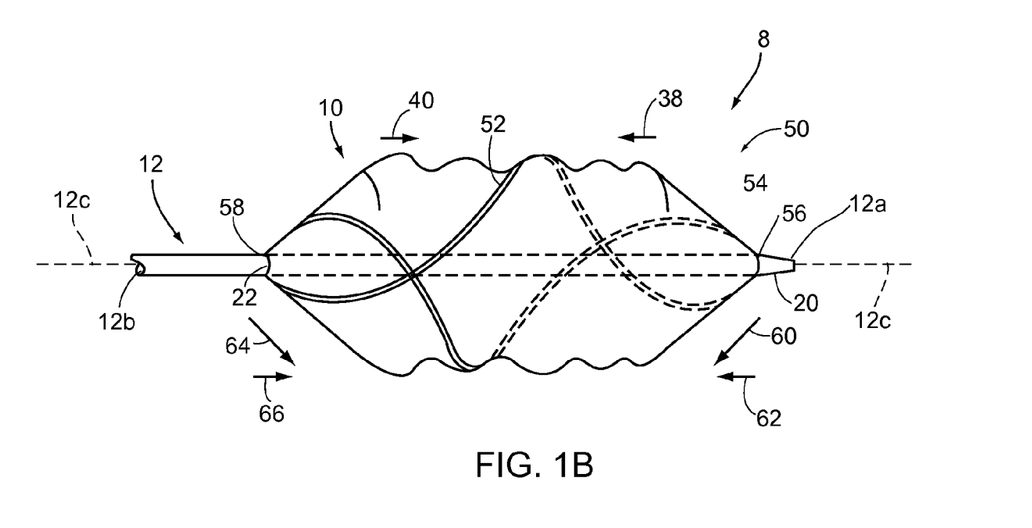
FIG. 1B shows a side view of a supporting structure including a pair of fibers wound as a braid, wrap, mesh, and the like around the balloon.

Turning to the drawings, FIGS. 1A and 1B show an exemplary embodiment of an apparatus 8 including an angioplasty catheter 12 carrying a balloon 10 with a supporting structure 50, e.g., including one or more wires or other fibers (two fibers 52, 54 shown), on an exterior of the balloon 10, as described further below. Generally, the catheter 12 includes a proximal end, e.g., including a handle or hub (not shown), a distal end 12b sized and/or shaped for introduction into a patient's body, and one or more lumens 12c extending therebetween, thereby generally defining a longitudinal axis 12d. For example, an inflation lumen 12c may be provided that communicates between a source of inflation media, e.g., a syringe (filled with inflation gas or fluid, such as saline) coupled to a handle or hub on the proximal end (not shown) and an interior of the balloon 10. Optionally, one or more additional lumens may be provided, e.g., a guidewire or instrument lumen extending between a port on the proximal end and an outlet in the distal end (not shown).

FIG. 1A shows an exemplary embodiment of an angioplasty balloon 10 positioned upon the catheter 12 (before placing the supporting structure 50 thereon, as shown in FIG. 1B), which may be directed between a contracted or delivery condition (not shown) and an expanded condition, shown in FIG. 1A. In the expanded condition, the balloon 10 may generally include a substantially cylindrical central section 18, and a proximal section 14 and a distal section 16 one or both of which may be conically shaped, tapered, or otherwise transition from the central section 18 to the outer wall of the catheter 12. Each of the respective sections 14, 16 may be attached to the distal end 12b of the catheter 12, e.g., at attachment locations 20, 22 using any number of securement mechanisms, e.g., one or more of bonding with adhesive, fusing, sonic welding, external collars, and the like (not shown).

The membrane of the balloon 10 may generally comprise a low-compliance or non-compliant material. The resulting non-compliant balloon 10 may be capable of withstanding relatively high-pressure inflation. As used herein, "non-compliant" means that the balloon 10 expands to a predetermined expanded shape, e.g., having a substantially uniform diameter along the central section 18, upon initial inflation, e.g., to a threshold pressure. If the pressure is increased beyond the threshold pressure, the size and/or shape of the balloon 10 may remain substantially unchanged, e.g., to allow the balloon 10 to apply the pressure radially outwardly to adjacent body structures surrounding the balloon 10. For example, the balloon membrane may be formed from substantially inelastic material configured to provide initial expansion and internal pressure and substantially maintain the predetermined expanded shape with minimal additional expansion, e.g., until a rupture or failure pressure is attained, which in an exemplary embodiment may be between about five and twenty atmospheres (5-25 atm).

Thus, when the balloon 10 is expanded, the balloon membrane may generate substantially equal forces in all parts of the balloon 10. For example, as represented in FIG. 1A, when the balloon 10 is inflated, e.g., via inflation media (such as an inflation gas or fluid such as saline), the fluid contained within the interior of the balloon 10 may exert a pressure 24 against the walls of the balloon membrane. The resultant force 26 exerted by the fluid pressure 24 upon the proximal section 14 of the balloon 10 may be seen projecting at an angle relative to the longitudinal axis of the catheter 12. A similar resultant force 28 exerted by the fluid pressure 24 upon the distal section 16 of the balloon 10 may also be seen projecting at an angle relative to the longitudinal axis of the catheter 12.

Each of the resultant forces 26, 28 includes a longitudinally-directed component of force 30, 32, respectively, which are oppositely directed relative to one another. In an equilibrium state, the longitudinally-directed component of force 30 on the proximal section 14 is equal and opposite to the sum of the reaction force 34 from the attachment between the catheter 12 and balloon 10 and from the longitudinally-directed tension 38 in the membrane wall of the balloon. Similarly, the longitudinally-directed component of force 32 on the distal section 16 is equal and opposite to the sum of the reaction force 36 from the attachment between the catheter 12 and the balloon 10 and from the longitudinally-direction tension 40 in the membrane wall of the balloon. Furthermore, in the absence of any longitudinally-directed tension, a circumferentially-directed tensile force 44 in the wall of the central section 18 generates a radially-directed force 46 to balance the outward force exerted by pressure 42.

As shown in FIG. 1B, the fibers 52, 54 of the supporting structure 50 may be wrapped helically around the balloon 10, e.g., as a braid, wrap, mesh, and the like, which may be carried by the balloon 10, e.g., substantially permanently attached to the balloon 10 and/or catheter 12 at one or more locations. For example, with the balloon 10 folded, rolled, or otherwise directed to the contracted condition, the fibers 52, 54 of the supporting structure 50 may be wrapped around and/or otherwise surround the outer surface of the balloon 10 and coupled to the distal end 12b of the catheter 12 and/or to ends of the balloon 10, as described elsewhere herein. Optionally, a preset axial tension may be applied to the fibers 52, 54 when wrapped around and maintained when the ends of fibers 52, 54 are attached relative to the catheter 12, e.g., to minimize the low-profile configuration of the supporting structure 50 and/or to constrain the balloon 10 in the contracted condition.

The supporting structure 50 is illustrated in this variation as two fibers 52, 54, which are positioned offset from one another about the periphery of the balloon 10 and both helically wound around the outer surface of the balloon 10, e.g., in opposite helical directions such that the fibers 52, 54 overlap one another one or more times along the length of the balloon 10. In this embodiment, any torsion induced by the fibers 52, 54 on the balloon 10 may offset one another, thereby providing a net twist on the balloon 10 that is substantially zero. Alternatively, the fibers may be wound in the same helical direction such that the fibers 52, 54 remain substantially offset from one another, e.g., by about one hundred eighty degrees (180°) (not shown). However, in this alternative, the fibers may apply a torsion around the balloon, which may cause undesired twisting.

The fibers 52, 54 are illustrated as being attached to either the catheter 12 and/or balloon 10 only at proximal and distal attachment locations 56, 58, e.g., adjacent respective balloon attachment locations 20, 22 while the lengths of the fibers 52, 54 between the attachment locations 56, 58 remain unattached to the balloon 10. Thus, the supporting structure 50 is disposed external to the balloon membrane and freely movable relative to the balloon outer surface, e.g., along at least the central region 18 and, optionally, along the end sections 14, 16. In exemplary embodiments, the ends of the fibers 52, 54 may be attached to the catheter distal end 12b over the attachment locations 20, 22 of the balloon membrane by one or more of wrapping ends of the fibers 52, 54 around the catheter 12, securing the ends to a collar on the catheter 12 (not shown), bonding with adhesive, fusing, heat welding or sonic welding the ends to the catheter 12 and/or to the ends of the balloon membrane, and the like. In an exemplary embodiment, the fibers 52, 54 may be formed from thermoplastic material capable of molding and/or fusion, e.g., such that ends of the fibers 52, 54 may be fused together to form a discrete collar at each end of the balloon membrane, e.g., to prevent fraying and/or facilitate attachment to the ends of the balloon 10. The supporting structure 50 may be applied to any number of different length catheters and various balloon structures in addition to those described herein.

The mechanical properties of a balloon 10 supported by a braid of fibers 52, 54 may depend on the ratio between the diameter of the maximally-expanded braid and the diameter of the maximally-expanded balloon. For example, if the diameter of the maximally-expanded braid (i.e., the maximum diameter to which the braid of fibers 52, 54 can be expanded on the catheter 12 independently of the balloon 10) is less than about one hundred thirty percent (130%) of the diameter of the maximally-expanded balloon 10, the braid may restrict balloon expansion, especially in the central region between the balloon ends. This ratio may result in the balloon assuming a dog-bone shape (i.e., larger towards the ends than the central region) on maximum expansion, with the most restricted central portion never achieving its full unrestricted diameter. If the diameter of the maximally-expanded braid is more than about one hundred fifty percent (150%) of the diameter of the maximally-expanded balloon, the balloon may not form a smooth arc of substantially uniform curvature (especially at high degrees of bending). Instead, the balloon may form a series of relatively straight segments connected by acute bends. Therefore, it may desirable to maintain the ratio of diameters of maximally-expanded braid to balloon between about one hundred twenty and one hundred sixty percent (120-160%) or between about one hundred thirty and one hundred fifty percent (130-150%).

Alternatively, while two fibers 52, 54 are illustrated, other variations of the supporting structure 50 may utilize more than two fibers, e.g., one or more sets of fibers wound in opposite directions and configured into a braid, wrap, mesh, and the like, e.g., between about two and one hundred fibers (2-100), ten and eighty (10-80), twenty and fifty (20-50), e.g., total fibers or in each direction, depending on the application, similar to other embodiments described elsewhere herein.

The catheter 12 itself may generally have a length between the proximal end and the distal end 12b, e.g., ranging between about eighty and one hundred fifty centimeters (80-150 cm) and having an outer diameter between about one and three millimeters (1-3 mm or 3-9 Fr). The balloon 10 may have a fusiform shape having an overall length between about ten and one hundred millimeters (10-100 mm) and having an expanded diameter along the central region 18 between two and twelve millimeters (2-12 mm). The balloon 10 may be attached on the distal end 12b of the catheter 12 adjacent a tapered or other atraumatic distal tip. The balloon 10 generally may be formed from low-compliance thermoplastic material, e.g., mid to high durometer PEBAX, nylon, or PET, and the like.

Generally, regardless of the number of fibers used or the configuration of the supporting structure 50, the fiber(s) may be formed from substantially inelastic material, i.e., such that each fiber does not substantially stretch or elongate axially, break, or otherwise fail during normal use conditions. In exemplary embodiments, the fiber(s) may be formed from a variety of materials, e.g., nylon, Nitinol, Kevlar Vectraon, Spectra, Dacron, Dyneema, Terlon (PBT), Zylon (PBO), Polyimide (PIM), ultra-high molecular weight polyethylene or polyester, and the like. The fiber(s) may be shaped into substantially round or flat, solid or hollow, ribbons, wires, or other filaments, e.g., by extrusion, weaving or braiding smaller filaments, machining, molding, etching, material deposition, and the like. In exemplary embodiments, the fibers may be a diameter or other maximum cross-sectional dimension between about 0.001 and 0.010 inch, e.g., between about 0.002 and 0.003 inch. The resulting fibers may be suitably flexible to be collapsed into a low-profile configuration when the balloon 10 is deflated to its contracted condition, e.g., for stent crimping or loading and/or intravascular delivery. The supporting structure 50 is also suitably flexible to be reconfigured into its deployed configuration when the balloon 10 is inflated to its expanded condition, e.g., for stent deployment or an angioplasty procedure, without substantial plastic or elastic elongation of each fiber along its length.

Optionally, the fiber(s) of the supporting structure 50 may be porous, e.g., such that one or more compounds may be loaded into the pores of the fiber(s), e.g., one or more therapeutic compounds. Alternatively, the fiber(s) may be coated with such compounds and/or other materials, such as radiopaque or other materials that may facilitate imaging the supporting structure using external imaging when the catheter 12 is introduced into a patient's body. In addition or alternatively, one or more compounds may be coated, embedded, or otherwise loaded on the outer surface of the balloon 10. When the balloon 10 is directed to the contracted condition, the supporting structure 50 around the balloon 10 may at least partially protect the compounds, e.g., from abrasion, and/or minimize exposure, e.g., until the balloon 10 is inflated and the fibers 52, 54 of the supporting structure 50 separate and expose the outer surface of the balloon 10, whereupon the compounds may be released into the surrounding tissue and/or within the body lumen.

Figure 10:
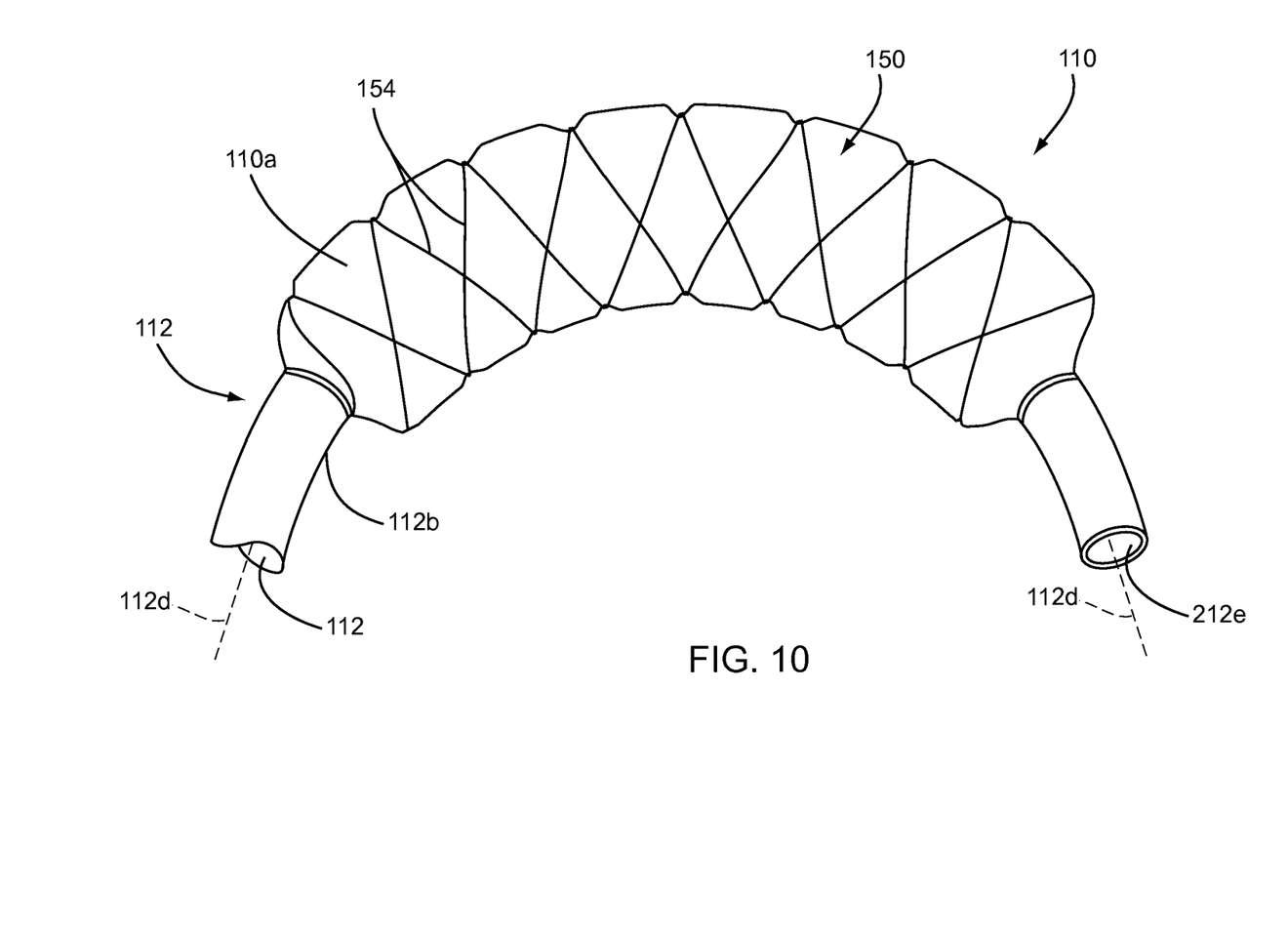
FIG. 10 is a side view of still another embodiment of a balloon catheter in which fibers of a supporting structure frictionally engage the outer surface of the balloon to resist the balloon straightening when inflated in a curved orientation.

A supporting structure 50 configured as a mesh of supporting fibers may bend in much the same way as a braided stent, e.g., by reorienting its fibers rather than stretching its fibers. Moreover, the supporting fibers may offer little resistance to bending or curving of the balloon 10 because little energy is needed to reorient such a mesh of fibers. Furthermore, increasing the number of fibers in a supporting structure 50 configured as a braid, wrap, or mesh may reduce or eliminate any bulging by portions of the balloon in the spaces between the fibers, e.g., by reducing the distance between the fibers and/or by further distributing any loads over the fibers, as described elsewhere herein. For example, as shown in FIG. 10, a catheter 112 may be provided that includes a balloon 110 carrying a supporting structure 150 including between about two and twenty (2-20) fibers 152 wound around the balloon 110 in a helical mesh.

Additionally, the supporting structure 50 may be attached at its proximal and distal attachment locations 56, 58 such that, when the balloon 10 is inflated, the supporting structure 50 may have a negligible or substantially no effect on the pressure-induced forces exerted on the balloon 10, as described elsewhere herein. In operation, as the balloon 10 is expanded to the expanded condition shown in FIG. 1B and the supporting structure 50 consequently reconfigures itself, the fibers of the supporting structure 50 may impart a tensile force along each of their respective longitudinal axes, as indicated by the tensile reaction forces 60, 64 shown in FIG. 1B. The reaction forces 60, 64 may each include in part a respective longitudinally-directed force component, as indicated by longitudinal reaction forces 62, 66. These reaction forces 62, 66 may urge the proximal and distal attachment locations 56, 58 of the supporting structure 50 towards one another, e.g., substantially parallel to the longitudinal axis 12d of the catheter 12, thereby urging the attachment locations 20, 22 of the balloon 10 towards one another as well as compressing axially at least the central region 18 of the catheter 12 (which is designed to shorten reversibly) between the two attachment locations 56, 58.

Hence, as the balloon 10 expands and is shortened by the supporting structure 50, the longitudinally-directed tension 38, 40 in the membrane wall of the balloon 10 may be relieved so that the tension 38, 40 no longer resists the longitudinally-directed component of force 30, 32. Because the expansion of the balloon 10 lengthens the helical path of the fibers of the supporting structure 50, the fibers may tighten and pull or urge the ends of the balloon 10 towards one another. This, in turn, enables the balloon 10 and supporting structure 50 to retain flexibility in bending or curving, e.g., to conform to the intravascular walls when the balloon 10 is inflated even at relatively high pressures. This is further in comparison to a balloon 10 without such a supporting structure 50 since such a balloon 10 would straighten upon inflation and not be able to bend or curve to the same degree of flexibility.

In the presence of a supporting structure 50, there is no fixed relationship between the tensile forces in the wall of the balloon 10 along a first direction and tensile forces in the wall along another direction, because the longitudinally directed component of force along the fibers of the supporting structure 50 over the balloon 10 may substitute for or substantially overcome the longitudinal component of tensile force along the balloon wall such that the longitudinal component along the balloon 10 may reduce or fall to zero or close to zero. The longitudinally off-loaded wall thus offers little resistance to bending or curving of the balloon 10.

In one variation, the catheter 12 may further comprise a "crumple zone" (not shown), e.g., on the distal end 12b between the ends of the balloon 10, which may allow the catheter 12 to reversibly shorten as the balloon 10 shortens. This may result in relatively more longitudinal redundancy, increased differential lengthening between opposite walls, and/or less resistance to bending. These crumple zones may be spring loaded (e.g., via any number of biasing mechanisms such as a slotted Nitinol hypotube, compression spring, and the like, not shown) to facilitate substantially returning to its initial length upon deflation of the balloon 10. Alternatively, the distal end 12b of the catheter 12 may have increased flexibility, e.g., between the attachment locations 20, 22 of the balloon 10, which may allow the distal end 12b to be directed from a generally linear to a helical or other nonlinear shape as the balloon 10 shortens, e.g., similar to the embodiment shown in FIG. 3A and described elsewhere herein.

Figure 2A:
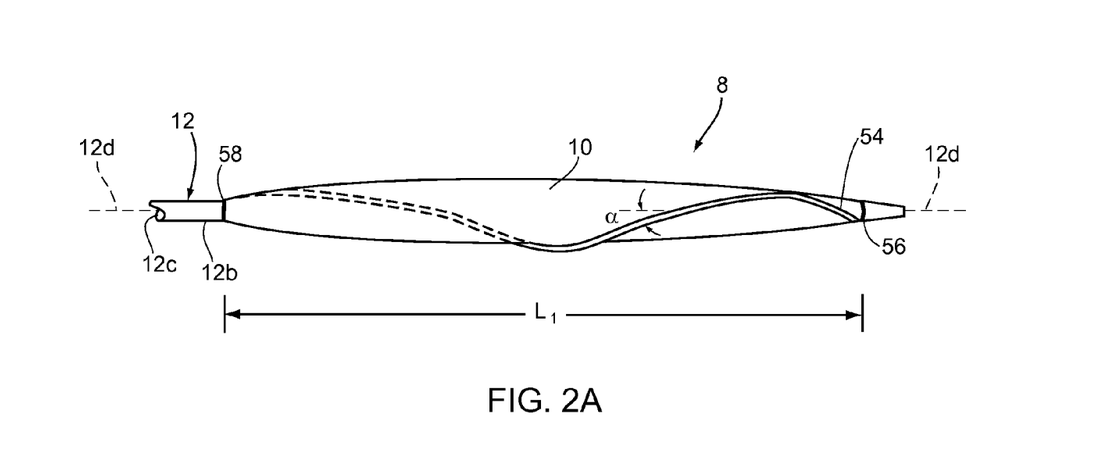
FIGS. 2A and 2B show side views of an alternative embodiment of a balloon with a supporting structure in its low-profile configuration when the balloon deflated and in its deployed configuration with the balloon inflated, respectively.
Figure 2B:
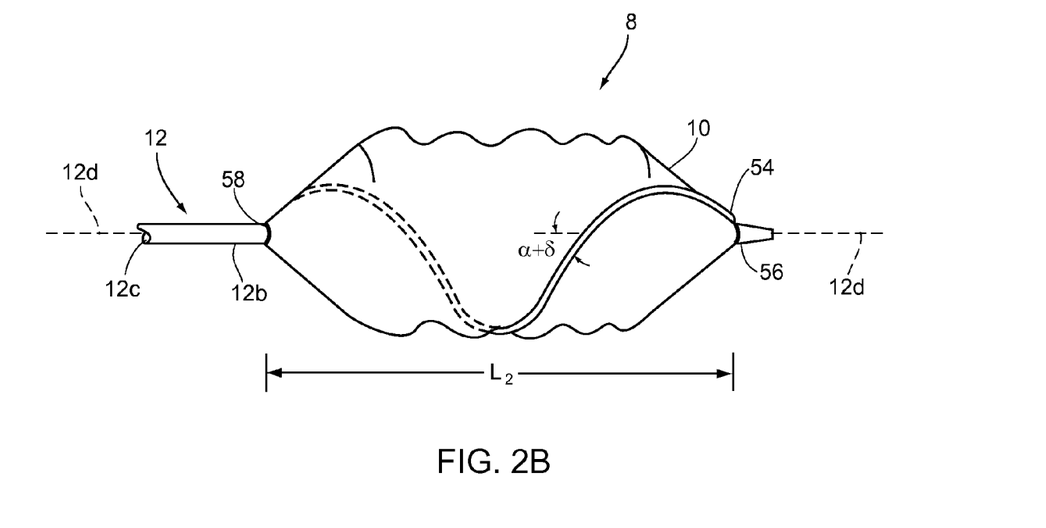

Turning to FIGS. 2A and 2B, another exemplary embodiment of an apparatus 8 is shown that includes a catheter 12 and a balloon 10 with supporting structure 50. In FIG. 2A, the balloon 10 is shown in its contracted or delivery condition with the supporting structure 50 in its low-profile configuration, while in FIG. 2B, the balloon 10 is shown in its expanded condition with the supporting structure 50 in its deployed configuration. In this embodiment, the supporting structure 50 includes a single fiber 54 attached at proximal and distal attachment locations 56, 58 on the balloon 10 and/or catheter 12 and wrapped or wound around the outer surface of the balloon 10. While a single fiber 54 is shown in this embodiment for simplicity, multiple fibers may be used as in other embodiments herein. The resulting low-profile configuration may have an overall deflated length of L1, as illustrated in FIG. 2A, and the fiber 54 may form an initial fiber braid angle α relative to the longitudinal axis 12d of the catheter 12. As the balloon 10 is inflated, as shown in FIG. 2B, the portion of the catheter 12 within the balloon 10 may become shortened as the helical path taken by the fiber 54 widens in diameter and forms an expanded and reconfigured fiber braid angle α+δ relative to the longitudinal axis 12d of the catheter 12, which is greater than the initial fiber angle α. Since the fiber 54 is made from a substantially inelastic material, the fiber 54 itself is unable to lengthen as its helical path widens and the tensile stress increases within the fiber 54. Accordingly, the balloon 10 is further shortened in length by its supporting structure 50 and is able to retain its flexibility due to the relieved tension along the membrane wall. The resulting inflated balloon length L2 is shown as being less than the initial deflated balloon length L1.

Figure 3A:
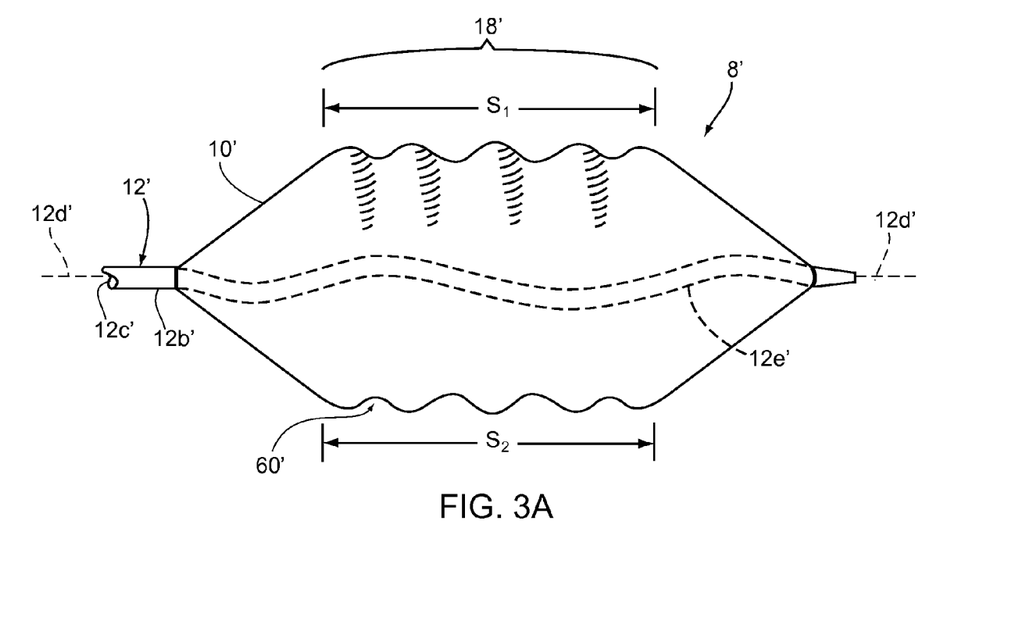
FIGS. 3A and 3B show side views of an inflated balloon having a supporting structure as it is inflated and bent or curved.
Figure 3B:
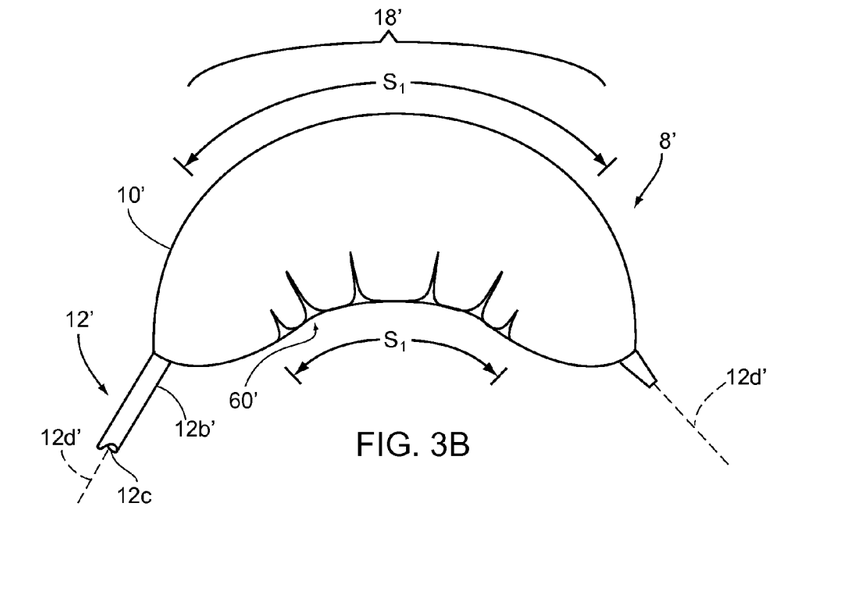

Turning to FIGS. 3A and 3B, yet another embodiment of an apparatus 8' is shown that includes a catheter 12' including an inflated balloon 10' thereon having a supporting structure (not shown for clarity) as it is inflated and bent or curved. As shown in FIG. 3A, when the balloon 10' expands and becomes shortened due to its supporting structure, the portion 12e' of the catheter 12' passing through the balloon interior may become longitudinally compressed and the balloon 10' itself may form one or more circumferentially oriented folds 60' along its length. These folds 60' may allow for differential lengthening between opposing walls of the cylindrical central section 18' of the balloon 10' thereby allowing the balloon 10' to bend or curve, e.g., as shown in FIG. 3B, when such a balloon 10' would normally be unable to due to the rigidity typically imposed when non-compliant balloons are expanded, as described further elsewhere herein. This is illustrated by the respective opposing side walls S1, S2 of the balloon 10' being substantially equal when the balloon 10' is inflated and straightened (as shown in FIG. 3A) but the first side wall length S1 becoming lengthened and the opposing second side wall length S2 becoming shortened when the balloon 10 is curved or bent (as shown in FIG. 3B) such that the first side wall length S1 forms the outer radius and the second side wall length S2 forms the inner radius of the curved balloon 10,' i.e., S1>>S2. Once the balloon 10' has been bent or curved, the supporting structure may enable the balloon 10' to remain in its bent or curved configuration unlike conventional high-pressure balloons.

Figure 4A:
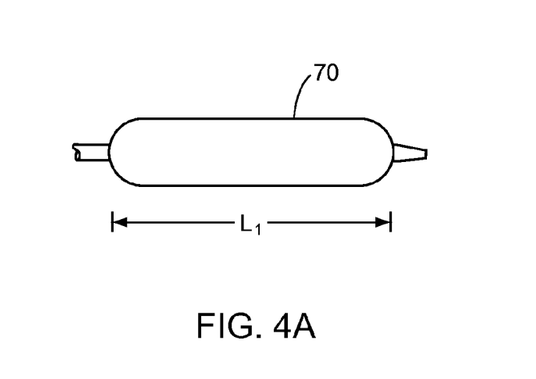
FIGS. 4A and 4B show side views of an exemplary angioplasty balloon having an inflated length without any supporting structure on the balloon.
Figure 4B:
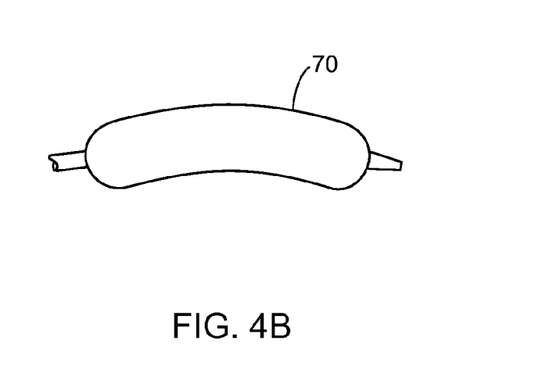
Figure 5A:
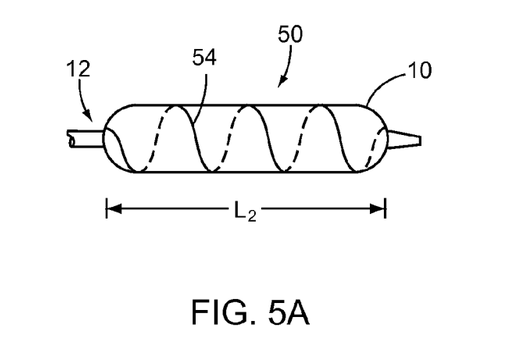
FIGS. 5A and 5B show side views of an inflated balloon having a supporting structure in its straightened and bent or curved configuration.
Figure 5B:
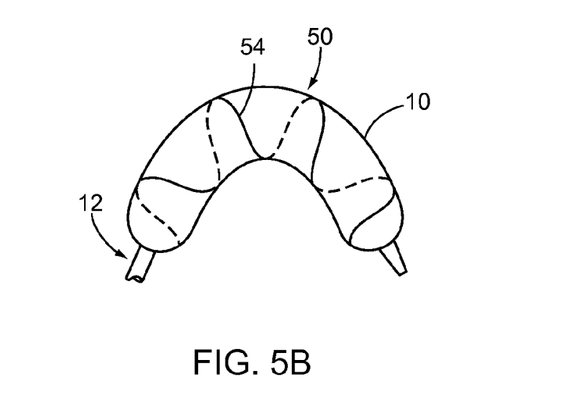

As a further illustration of the effect of the supporting structure on an inflated balloon as described herein, FIGS. 4A and 4B show side views of an exemplary conventional angioplasty balloon 70 having an inflated length L1 without any supporting structure integrated with the balloon 70. FIG. 4B illustrates minimal bending or curving of the balloon 70 relative to its straightened configuration when any off-axis force is imparted to the balloon 70, such as when the balloon 70 is inflated within a curved vessel. This is in contrast to a catheter 12 having a supporting structure 50 integrated with a balloon 10, as shown in the side view of FIGS. 5A and 5B, e.g., which may be similar to the apparatus 8 shown in FIGS. 2A and 2B or to other embodiments herein. Although the single fiber 54' is shown as being helically positioned over the balloon 10, this is intended to be exemplary and any number of additional fibers may be utilized for the supporting structure, as described elsewhere herein.

When inflated at similar high pressures to the unsupported balloon 70, the balloon 10 having the supporting structure 50 may cause the overall balloon length to shorten slightly during inflation, relieving tension in the balloon 10 and distal end 12b of the catheter 12 within the balloon 10, and providing redundancy that allows differential lengthening between the inner and outer aspects of the balloon 10 when deployed in a curved body lumen. For example, the unsupported balloon shown in FIG. 4A may have a length L1 that remains substantially unchanged during inflation. In contrast, the balloon 10 with supporting structure 50 may have a deflated length similar to L1, yet, upon inflation, may have a length L2 which is shorter than the initial length L1. Moreover, the resulting balloon 10 of FIGS. 5A and 5B may substantially retain its flexibility in bending or curving, as shown in the side view of FIG. 5B, unlike the unsupported balloon 70, which resists bending as shown in FIG. 4B.

Figure 6:
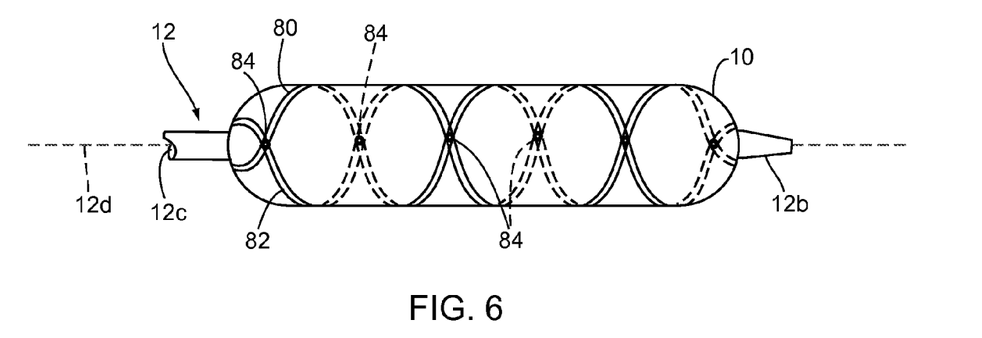
FIG. 6 shows a side view of a variation where the supporting structure may be configured with, e.g., two or more fibers, which are attached or connected to one another at intersecting points.

In yet additional variations, a supporting structure may be configured in a number of different configurations over a balloon. FIG. 6 shows a side view of an exemplary embodiment where the supporting structure may be configured with two or more fibers, e.g., two fibers 80, 82, shown wound in opposite directions relative to one another around a balloon 10, which are attached or otherwise coupled to one another at intersecting points 84. For example, at the intersecting points 84 where the fibers overlap or otherwise intersect one another as they extend helically around the balloon 10, the fibers 80, 82 may be tied, secured, looped, bonded, attached, or otherwise coupled to one another such that the fibers 80, 82 are able to rotate or twist around the intersecting points 84 as the balloon 10 is expanded. In one embodiment, the fibers 80, 82 may be coupled at each of the intersecting points 84, or alternatively, the fibers 80, 82 may be coupled at only some, e.g., every other or every third, intersecting point 84. Although two fibers 80, 82 are shown, a single fiber or more than two fibers may be utilized, e.g., as described elsewhere herein.

Figure 7:
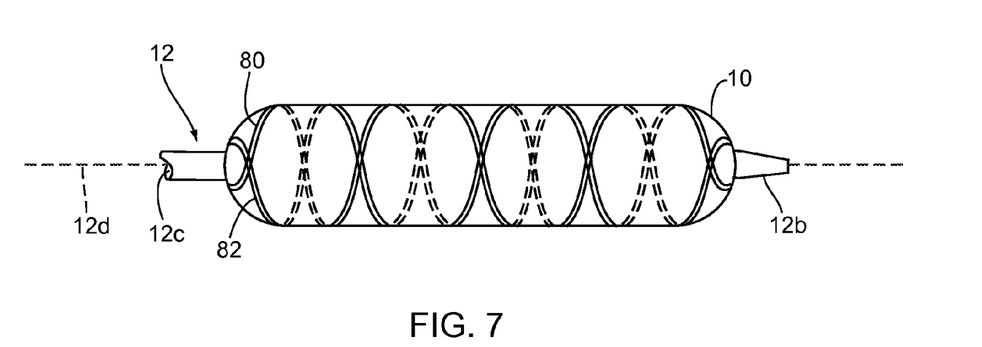
FIG. 7 shows yet another variation where the fibers may be formed to have a relatively higher pitch or angle relative to the longitudinal axis of the catheter.

FIG. 7 shows yet another variation where the fibers 80, 82 may be formed to define a relatively higher pitch or angle relative to the longitudinal axis 12d of the catheter 12. As the balloon 10 expands to its expanded condition, the supporting structure may define a relatively higher density structure because of the additional windings the fibers 80, 82 undergo. A supporting structure having a relatively lower pitch or winding angle may provide little resistance to expansion of the balloon 10 while a relatively higher pitch or winding angle may provide for a balloon assembly having increased flexibility. The higher pitch may also increase the ratio of length change to diameter as the balloon 10 is expanded, e.g., compared to the embodiment shown in FIG. 6.

Figure 8:
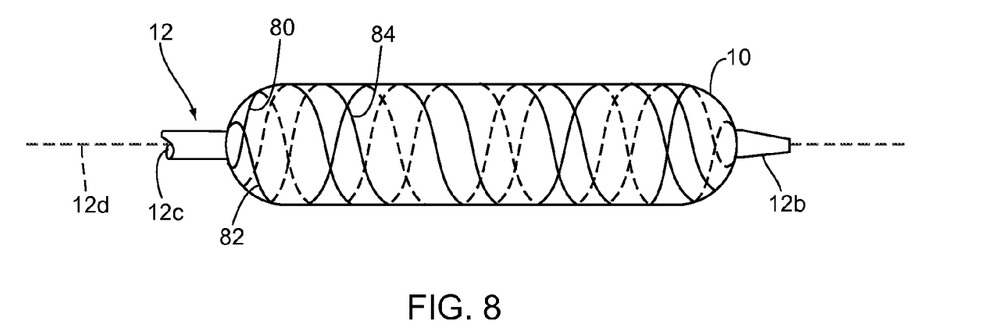
FIG. 8 shows a side view of yet another variation where three fibers are used to form the supporting structure.

FIG. 8 shows a side view of yet another embodiment where three fibers 80, 82, 84 are used to form the supporting structure. Optionally, in this embodiment as in each of the others, the fibers 80, 82, 84 may be tied, secured, attached, or otherwise coupled to one another at one or more intersecting points or the individual fibers may simply overlie one another uncoupled to one another, e.g., in an over-under braiding or other pattern.

Figure 9:
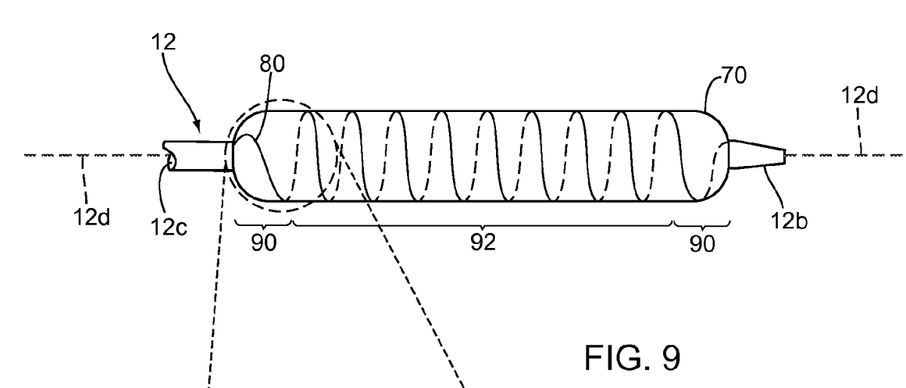
FIG. 9 shows yet another variation illustrating how a fiber may be used to form regions along the balloon with varying pitch or winding density.
Figure 9A:
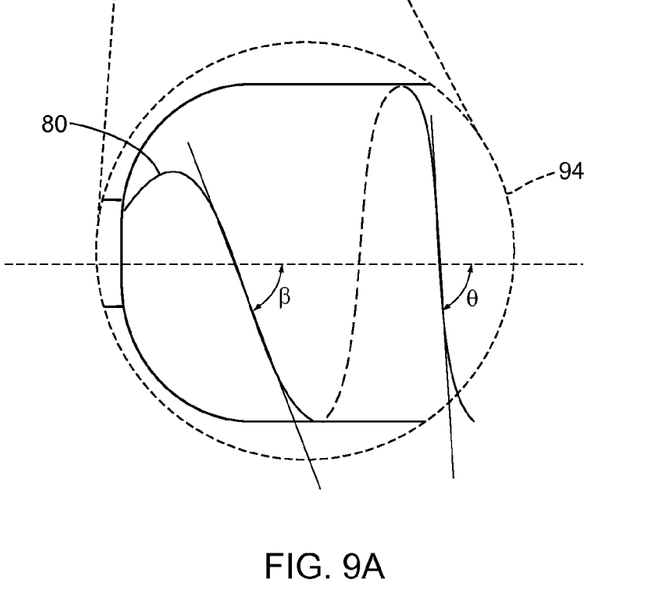
FIG. 9A is a detail of a first end of the balloon of FIG. 9.

FIG. 9 shows yet another embodiment illustrating how a fiber 80 of a supporting structure may be used to form regions along the balloon 10 with varying pitch, winding density, and/or other mechanical properties. For example, a first portion 90 of the balloon 10 may have the fiber 80 define a relatively lower pitch or winding angle relative to the longitudinal axis 12d of the catheter 12, as shown in FIG. 9A. A second portion 92 of the balloon 10 may have the fiber 80 define a relatively higher pitch or winding angle, as shown, relative to the first portion 90 and to the longitudinal axis 12d of the catheter 12. In this embodiment as well as others described herein, any of the embodiments described may incorporate one or more regions with varying pitch of fiber angle depending upon the desired flexing or other mechanical properties of the balloon 10. Moreover, the supporting structure may be configured to have two or more regions with varying pitch or winding angle where each of the regions may also be optionally varied in length along the balloon 10 as well.

Optionally, in any of the embodiments, one or more layers may be provided over the supporting structure (not shown). For example, with reference to the apparatus 8 shown in FIGS. 1A and 1B, a relatively thin outer layer of elastic material (not shown) may be provided over the supporting structure that is attached to the catheter 12, e.g., at or beyond the ends 20, 22 of the balloon 10. The outer layer may be formed from lubricious material or may include a lubricious coating on one or both of its inner and outer surfaces. Thus, during expansion of the balloon 10 and the resulting reconfiguration of the supporting structure 50, the outer layer may provide a transition between the supporting structure 50 and a stent or other prosthesis (not shown) loaded over the balloon 10. As the fiber(s) of the supporting structure change angle and/or otherwise reconfigure during expansion, any torsional or other circumferential forces may be absorbed by the outer layer and not transmitted to the prosthesis, thereby maintaining the prosthesis in its original shape during expansion.

During use, any of the apparatus herein may be used to perform a medical procedure within a patient's body. For example, with reference to the apparatus 8 shown in FIGS. 1A and 1B, an angioplasty procedure may be performed to dilate or otherwise treat a stenosis or other lesion within a patient's vasculature. With the balloon 10 in its contracted condition (not shown), the distal end 12b of the catheter 12 may be introduced into the patient's vasculature from a percutaneous entry site, e.g., in the patient's femoral, carotid, or other periphery vessel, e.g., in conjunction with a guide catheter, guidewire, and/or other instruments (not shown), similar to conventional interventional procedures. The distal end 12b may be advanced and/or otherwise directed from the proximal end of the catheter 12 to position the balloon 10 across the lesion. The balloon 10 and supporting structure 50 may be sufficiently flexible to allow advancement through tortuous anatomy, e.g., even within a lesion located within a curved or other nonlinear vessel.

Once positioned within the lesion, the balloon 10 may be inflated to direct the balloon 10 to the expanded condition, thereby causing the supporting structure 50 to reconfigure to its deployed configuration. If the balloon 10 is positioned within a curved lesion, the supporting structure 50 may substantially maintain the balloon 10 in the curved shape corresponding to the lesion. For example, the supporting structure 50 may cause the balloon 10 to shorten and/or otherwise reconfigure, e.g., generating one or more folds within an inner radius and/or other regions of the balloon 10, thereby providing sufficient flexibility to conform to the curved shape of the lesion despite the non-compliant material of the balloon 10.

Optionally, before a procedure, the balloon 10 may be prepared to cause the balloon 10 to exhibit "shape-memory," e.g., biasing the balloon 10 to a desired curved or other shape. For example, immediately before the procedure, the balloon 10 may be inflated to a fully expanded (e.g., substantially straight) condition, while bent into a desired curved shape (e.g., a simple curve having a desired radius of curvature or a more complicated shape, if desired), thereby reconfiguring the supporting structure 50 further to maintain the balloon 10 in the curved shape. For example, the fibers 52, 54 may slide along the outer surface of the balloon 10 to accommodate the curved shape and/or one or more folds may be formed in the balloon 10. The balloon 10 may then be deflated back to the contracted condition.

Having been expanded in a curved shape, the balloon 10 adopt substantially the same shape upon re-inflation, despite interval deflation and reconfiguration (in the deflated state). A new shape (in the inflated state) may be imprinted on the balloon, if desired, e.g., by forcibly bending the inflated balloon, or by bending the uninflated balloon and re-inflating it while maintaining the new shape.

This feature may be useful when luminal instrumentation must traverse a curved path. For example, it is often difficult to induce sufficient bending in a conventional dilator to allow passage of a sheath around a bend, branch point, or narrowing. Under these circumstances, a fixed bend in the dilator may be moderately helpful if it were not so difficult to introduce through straight segments of the corporeal lumen or straight segments of the sheath. An uninflated shape-memory balloon may be flexible enough for easy insertion into an obstructing lesion, just beyond the tip of the sheath where balloon inflation induces bending. The sheath may then be advanced with, or over, the suitably sized balloon, past the obstructing lesion and into the target lumen.

One potential advantage of the balloon 10 and supporting structure 50 described herein is that the supporting structure 50 may facilitate substantially uniform expansion of the balloon 10. For example, with the supporting structure 50 carried by the balloon 10, the balloon 10 may expand substantially uniformly throughout its length during inflation, e.g., unlike a typical non-compliant balloon, which tends to expand to full diameter in one or two locations (e.g., at the ends) before propagating down the balloon (e.g., towards the middle of the balloon).

In addition or alternatively, the fibers 52 of the supporting structure 50 may decouple the unfurling balloon from the inner surface of an artery within which the balloon 10 is inflated, or from the inner surface of a stent (not shown) if carried on the balloon 10. In the absence of a stent, this effect may protect the artery from torsion and dissection since the balloon 10 may be free to unfurl within the surrounding fibers 52 of the supporting structure 50. In the presence of a stent, this effect may increase the security of stent attachment, e.g., since the balloon 10 may be free to slide within the supporting structure 50 as it unfurls and expands, thereby minimizing torsional forces on a stent carried around the supporting structure 50. In contrast, a conventional angioplasty balloon may not attach itself securely to the stent without limiting the necessary rotation that has to occur for a noncompliant balloon to open. Such a configuration may facilitate delivery of multiple independent stents carried on a single balloon, e.g., as disclosed in application Ser. No. 14/133,542, filed Dec. 18, 2013, the entire disclosure of which is expressly incorporated by reference herein.

In an alternative embodiment, optionally, the outer surface of the balloon 10 may be configured to enhance engagement between the supporting structure 50 and the balloon 10 during expansion, e.g., to secure the balloon 10 in a curved shape within a similar shaped lesion. For example, the outer surface of the balloon 10 may include a high friction treatment or coating such that the supporting structure 50 may frictionally engage the balloon 10 during expansion to maintain the curved shape and resist the balloon 10 straightening during expansion, which may otherwise cause undesired stress within the vessel within which the balloon 10 is expanded.

For example, FIG. 10 shows a catheter 112 including a balloon 110 and supporting structure 150, generally constructed similar to other embodiments herein. The supporting structure 150 includes a plurality of substantially inelastic fibers 154 woven into a braid. Although the embodiment shown includes only a single fiber 154 wound in each helical direction, a more dense braid or mesh may be provided, if desired, e.g., including between two and ten fibers wound in each direction. Inflation of the balloon 110 exerts an outward force on the fibers 154 of the supporting structure 150, thereby tensioning the fibers 154 between their attachment points proximal and distal to the balloon 110. Thus tensioned, the fibers 154 of the supporting structure 150 may indent slightly into the outer surface 110a of the balloon 110, e.g., creating a slight quilting of the balloon surface (exaggerated in FIG. 10 for effect).

Optionally, the outer surface 110a of the balloon 110 may include a high friction coating, texture, or other features to increase engagement between the fibers 154 and the balloon 110. The resultant friction between the fibers 154 and the balloon 150 may substantially fix both of them in position when the balloon 110 is inflated, e.g. within a curved or otherwise shape lumen, which may resist bending or subsequent straightening of the balloon 110 and the distal end 112b of the catheter 112 within balloon 110. Optionally, the distal end 112b of the catheter 112 may be constructed to accommodate the curved shape while ensuring that a working lumen 112c through the catheter 112 remains open, e.g., to accommodate one or more instruments therethrough. With the frictional engagement between the fibers 154 and the balloon 110, the distal end 112b of the catheter 112 may transition from flexible to inflexible, which may be useful in an interventional procedure that requires an abrupt change in direction from the site of access to the site of intervention.

Figure 11:
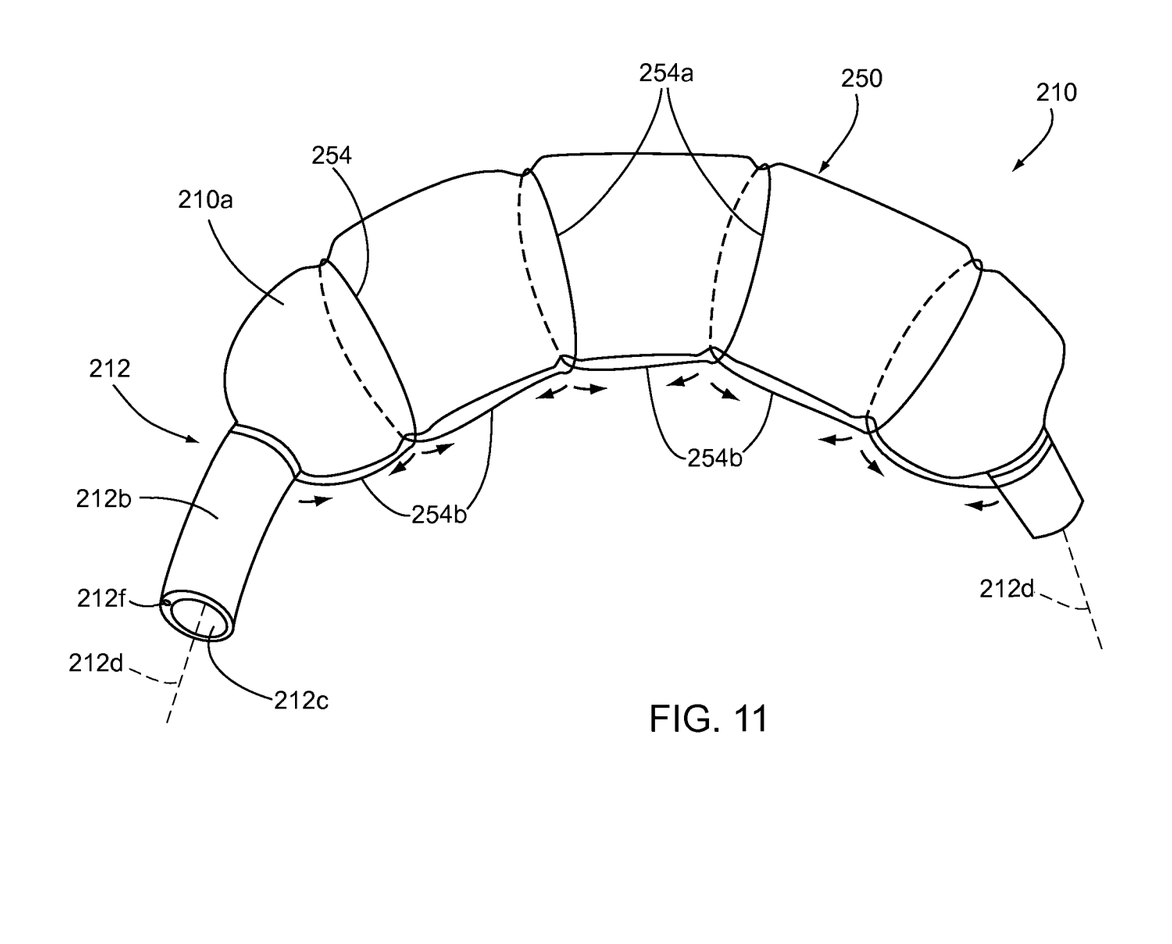
FIG. 11 is a side view of yet another embodiment of a balloon catheter including a supporting structure that includes an asymmetrical arrangement of one or more fibers that bias the balloon to bend to a curved shape when inflated.

Turning to FIG. 11, in another embodiment, a catheter 212 may be provided in which the supporting structure 250 may bias the balloon 210 to expand in a predetermined curved shape when inflated. Generally, the catheter 212 includes a proximal end (not shown), a distal end 212b, a working lumen 212c, an inflation lumen 212f, and a longitudinal axis 212d, similar to other embodiments herein. In addition, the catheter 212 includes a balloon 210 and a supporting structure 250, which may be constructed similar to other embodiments herein. As shown, the supporting structure 250 may include a single fiber 254 disposed asymmetrically around the outer surface 210a of the balloon 210, e.g., such that the fiber 254 defines a plurality of circumferential loops 254a that extend around the outer surface of the balloon 210 that are connected together by a single longitudinal or axial segment 254b between adjacent loops 254a with the longitudinal segments 254b aligned with one another along one side of the balloon 210.

As a result of this configuration of the fiber 254, the fiber 254 may be tensioned when the balloon 210 is inflated, to apply more traction to one side of the balloon 210 than an opposite side, and causing the catheter 212 to bend, e.g., around the side including the longitudinal segments 254b, as shown in FIG. 11. Thus, the balloon 210 may be positioned within a curved lesion and then inflated with the fiber 254 maintaining the distal end 212b in a curved orientation as the balloon 210 is inflated. Alternatively, the balloon 210 may be expanded to deflect the distal end 210 from a substantially straight to a curved configuration, e.g., to facilitate accessing body lumens or other passages within a patient's body. For example, the distal end 212b may be curved or bent to direct an outlet 212e of the working lumen 212c towards a branch or other passage, thereby allowing a guidewire, catheter, and/or other device to be advanced from the working lumen 212c into the target passage, e.g., to facilitate branch catheterization.

Optionally, the catheter 212 may include one or more markers, e.g., formed from radiopaque, echogenic, or other materials (not shown), that may be provided at desired locations on the distal end 212b, balloon 210, and/or fiber 254 to facilitate identifying the location and/or orientation of the balloon 210 and fiber 254 using external imaging, e.g., fluoroscopy, ultrasound, and the like. For example, a marker may be provided that is disposed asymmetrically on the balloon 210, e.g., aligned with the longitudinal segments 254b of the fiber 254 to facilitate identifying the orientation of the fiber 254 within a body passage. Thus, the user may rotate the catheter 212 from its proximal end to rotate the balloon 210 and fiber 254 until the longitudinal segments 254b are oriented closer to a branch or curve towards which the distal end 212b is to be directed.

In another option, a stent or other prosthesis (not shown) may be carried on any of the catheters herein, e.g., on the catheter 12 of FIGS. 1A and 1B over the balloon 10, and the prosthesis may be expanded and/or otherwise deployed within the lesion when the balloon 10 is expanded.

Optionally, the balloon 10 (of any of the embodiments herein) may be deflated and inflated one or more times, e.g., within the lesion and/or after positioning to one or more other locations within the patient's vasculature. Once the procedure is completed, the balloon 10 may be deflated to the contracted condition, thereby reconfiguring the supporting structure 50 to the low-profile configuration, and the catheter 12 may be removed from the patient's body.

The applications of the devices and methods discussed above are not limited to angioplasty balloons but may include any number of other inflatable balloon applications. Modification of the above-described assemblies and methods for carrying out the invention, combinations between different variations as practicable, and variations of aspects of the invention that are obvious to those of skill in the art are intended to be within the scope of the claims.

I claim:

1. An apparatus for performing procedure within a patient's body, comprising:
    a tubular member comprising a proximal end, a distal end sized for introduction into a patient's body, and a longitudinal axis extending therebetween;
    a low-compliance balloon carried on the distal end comprising a central region and end regions transitioning from the central region to attachment locations on the distal end, the balloon expandable from a contracted condition to an expanded condition; and
    a supporting structure comprising a plurality of substantially inelastic fibers extending helically around an outer surface of the balloon, the fibers comprising first ends fixedly attached to the distal end at first locations such that the first ends cannot move relative to the distal end and second opposite ends fixedly attached to the distal end at second locations such that the second ends cannot move relative to the distal end, while intermediate regions of the fibers are movable relative to the central region of the balloon such that, during expansion of the balloon, the end regions of the balloon and the first and second locations move towards one another and shorten an overall length of the balloon to enable the balloon and supporting structure to retain flexibility in bending or curving to conform to intravascular walls or prevent straightening of the balloon when the balloon is expanded,
    wherein one or more of the plurality of fibers are wound helically in a first direction and one or more of the plurality of fibers are wound helically in a second direction such that the fibers overlap one another at one or more intersecting locations without being coupled to one another at the one or more intersecting locations.

2. The apparatus of claim 1, wherein the intermediate regions of the fibers are configured to slide along the outer surface during expansion of the balloon to increase a helical angle of the fibers relative to the longitudinal axis, thereby causing the end regions of the balloon and the first and second locations to move towards one another and shorten an overall length of the balloon.

3. The apparatus of claim 1, wherein the end regions taper to ends attached to the distal end of the tubular member and wherein the fibers are attached to the distal end of the tubular member such that the intermediate regions of the fibers are slidable along the end regions of the balloon.

4. The apparatus of claim 1, wherein the plurality of fibers are formed as a braid around the outer surface of the balloon.

5. The apparatus of claim 4, wherein the fibers are formed from thermoplastic material and wherein respective ends of the fibers are attached together to form collars adjacent the end regions of the balloon.

6. The apparatus of claim 4, wherein a ratio of the diameter of the supporting structure when maximally-expanded to the diameter of the balloon when maximally-expanded is between about one hundred thirty and one hundred fifty percent (130-150%).

7. The apparatus of claim 4, wherein the braid is configured to cause the balloon to shorten between about five and twenty percent (4-20%) when the balloon is expanded from the contracted condition to the expanded condition.

8. The apparatus of claim 4, wherein the braid is configured to cause the balloon to shorten between about ten and thirty percent (10-30%) when the balloon is expanded from the contracted condition to the expanded condition.

9. The apparatus of claim 1, wherein the balloon is configured to form one or more circumferentially oriented folds as the balloon is expanded and shortens, thereby allowing the balloon to bend or curve.

10. An apparatus for performing procedure within a patient's body, comprising:
    a tubular member comprising a proximal end, a distal end sized for introduction into a patient's body, and a longitudinal axis extending therebetween;
    a balloon carried on the distal end comprising a central region and proximal and distal end regions transitioning from the central region to attachment locations on the distal end, the balloon expandable from a contracted condition to an expanded condition; and
    a supporting structure comprising a plurality of substantially inelastic fibers formed as a braid extending helically around an outer surface of the balloon, the fibers comprising first ends fixedly attached at first locations to one of the balloon end region and the tubular member distal end adjacent the balloon proximal end region and second opposite ends fixedly attached at second locations to one of the balloon distal end region and the tubular member distal end adjacent the balloon distal end region such that the first and second ends cannot move relative to the distal end while the intermediate regions of the fibers are slidable over the central region of the balloon during expansion of the balloon, thereby causing the proximal and distal end regions of the balloon and the first and second locations to move towards one another and shorten an overall length of the balloon and enable the balloon and supporting structure to retain flexibility in bending or curving to conform to intravascular walls or prevent straightening of the balloon when the balloon is expanded.

11. The apparatus of claim 10, wherein one or more of the plurality of fibers are wound helically in a first direction and one or more of the plurality of fibers are wound helically in a second direction such that the fibers overlap one another at one or more intersecting locations without being coupled to one another at the one or more intersecting locations.

12. The apparatus of claim 10, wherein the proximal and distal end regions taper to ends attached to the distal end of the tubular member and wherein the first and second ends of the plurality of fibers are attached to the distal end of the tubular member such that the intermediate regions of the fibers are slidable along the proximal and distal end regions of the balloon.

13. The apparatus of claim 10, wherein the fibers are formed from thermoplastic material and wherein respective first and second ends of the fibers are attached together to form collars adjacent the proximal and distal end regions of the balloon.

14. The apparatus of claim 10, wherein a ratio of the diameter of the supporting structure when maximally-expanded to the diameter of the balloon when maximally-expanded is between about one hundred thirty and one hundred fifty percent (130-150%).

15. The apparatus of claim 10, wherein the braid is configured to cause the balloon to shorten between about five and twenty percent (4-20%) when the balloon is expanded from the contracted condition to the expanded condition.

16. The apparatus of claim 10, wherein the balloon is formed from low-compliance material.

17. The apparatus of claim 10, wherein the balloon is formed from non-compliant material.

18. The apparatus of claim 10, wherein the proximal and distal end regions taper to the attachment locations of the tubular member and wherein the fibers are attached to the distal end of the tubular member adjacent the attachment locations such that the intermediate regions of the fibers are slidable along the proximal and distal end regions of the balloon.

19. The apparatus of claim 10, wherein the distal end of the tubular member between the first and second attachment locations is configured to foreshorten during expansion of the balloon to accommodate bending of the distal end.

20. The apparatus of claim 19, wherein the distal end of the tubular member comprises a crumple between the attachment locations of the balloon configured to reversibly shorten as the balloon foreshortens during expansion.

* * * * *